(12) United States Patent
Lazzaro et al.

(10) Patent No.: US 7,192,416 B1
(45) Date of Patent: Mar. 20, 2007

(54) FRONT LOAD PRESSURE JACKET SYSTEM WITH GROOVED SYRINGE HOLDER

(75) Inventors: Frank A. Lazzaro, Pittsburgh, PA (US); Michael A. Spohn, Butler, PA (US); Robert J. Ashcraft, Jr., Butler, PA (US)

(73) Assignee: Medrad, Inc., Indianola, PA (US)

( * ) Notice: Subject to any disclaimer, the term of this patent is extended or adjusted under 35 U.S.C. 154(b) by 734 days.

(21) Appl. No.: 10/325,494

(22) Filed: Dec. 20, 2002

(51) Int. Cl.
*A61M 1/00* (2006.01)

(52) U.S. Cl. ...................................... 604/152; 604/131
(58) Field of Classification Search ................ 604/131, 604/151, 152, 154, 156, 181, 187, 188, 218; 128/DIG. 1, 6; 600/431, 432
See application file for complete search history.

(56) References Cited

U.S. PATENT DOCUMENTS

| | | | | |
|---|---|---|---|---|
| 4,516,969 A | * | 5/1985 | Kintner | ...................... 604/187 |
| 4,677,980 A | | 7/1987 | Reilly et al. | |
| 5,300,031 A | | 4/1994 | Neer et al. | |
| 5,383,858 A | | 1/1995 | Reilly et al. | |
| 5,535,746 A | * | 7/1996 | Hoover et al. | .............. 600/432 |
| 5,779,675 A | | 7/1998 | Reilly et al. | |
| 5,800,397 A | | 9/1998 | Wilson et al. | |
| 5,873,861 A | | 2/1999 | Hitchins et al. | |
| 5,947,935 A | | 9/1999 | Rhinehart et al. | |
| 6,159,161 A | * | 12/2000 | Hodosh | ...................... 600/561 |
| 6,368,307 B1 | * | 4/2002 | Ziemba et al. | .............. 604/218 |
| 6,582,399 B1 | * | 6/2003 | Smith et al. | ................ 604/152 |

* cited by examiner

*Primary Examiner*—Nicholas Lucchesi
*Assistant Examiner*—Theodore J. Stigell
(74) *Attorney, Agent, or Firm*—Gregory L. Bradley; Christian E. Schuster (57) ABSTRACT

The fluid injection apparatus includes a syringe, an injector, and a pressure jacket. The syringe has a cylindrical body with an injection section at a distal end and a plurality of outward extending retaining flanges at a proximal end. The injector has an injector housing defining a central opening and an injector drive piston extendable through the central opening for imparting motive forces to a syringe plunger disposed within the syringe. The pressure jacket secures the syringe during an injection procedure. The pressure jacket has a wall defining a plurality of longitudinally extending grooves in an inner surface thereof configured to receive the retaining flanges of the syringe. The grooves cooperate with a plurality of transversely extending slots defined in the inner surface of the pressure jacket wall. The engagement of the retaining flanges in the slots via the grooves secures the syringe in the pressure jacket.

23 Claims, 6 Drawing Sheets

FRONT LOAD PRESSURE JACKET SYSTEM WITH GROOVED SYRINGE HOLDER

BACKGROUND OF THE INVENTION

1. Technical Field of the Invention

This invention relates generally to pressure jacket systems for securing a syringe to an injector, to syringes for use with pressure jackets systems and to methods of loading syringes in and removing syringes from pressure jacket systems. More specifically, the invention relates to front-loading pressure jacket systems and methods for allowing front loading and removal of syringes therefrom, and to syringes of special construction for use with, for example, pressure jackets.

2. Description of Related Art

In the medical field, patients are often injected with fluids in procedures such as angiography, computed tomography (CT), and magnetic resonance imaging (MRI). In such procedures, which require controlled injection of relatively large volumes of fluid into a patient, a catheter is used as a conduit for the fluid, which is connected to the syringe(s) by a connector tube. The syringe(s) is mounted on a motorized injector having an injector head.

For compatibility with injectable fluids, syringes may be made of glass or polymeric materials, such as polypropylene, with a certain minimum wall thickness. The thickness is critical as typical pressures of up to 1200 p.s.i. (i.e., in angiographic procedures) are used to inject the fluids into a patient.

Pressure jackets are known in the art in at least two varieties, breech or rear loading and front-loading, for substantially enclosing and retaining syringes while in use. A pressure jacket serves to limit radial expansion of a syringe, which may lead to bursting or to leaks of the pressurized fluid around the seal(s) of the syringe plunger. Another function of a pressure jacket is to prevent forward motion of the syringe. For example, typically a force of 2000 pounds is required to restrain the forward motion of a 200 ml syringe with a cross section of 1.7 in$^2$ at 1200 p.s.i.

U.S. Pat. No. 4,677,980, the contents of which are incorporated herein by reference, discloses an angiographic injector apparatus in which syringes are rear loaded into a pressure jacket of the injector. More specifically, the apparatus comprises a rotatable turret that carries a pair of the pressure jackets and which is rotatable so that when one of the pressure jackets, into which a syringe has been rear loaded, is in an injection position, the other pressure jacket is in a position in which an associated syringe can be rear loaded. Subsequently, when injection of contrast media from the first syringe is completed, the turret is rotated to move the first syringe to an unloading-loading position, with the second pressure jacket and the syringe concurrently being moved into the injection position.

A disadvantage of rear loading, pressure jacketed injectors is that, after an injection, the patient tubing typically must be disconnected from the syringe before the syringe can be extracted from the rear of the pressure jacket and discarded. Not only does this operation expend valuable operator time, but fluids, such as contrast fluid and blood, may drip or spill from the syringe or the tubing after the tubing is removed from the syringe, thereby creating a potentially unsafe or hazardous condition. Additionally, fluid spilled during loading and purging air from the syringe may migrate inside the pressure jacket and the injector, and require cleaning.

Motivated at least in part by this concern, front-loading injectors (pressure jacketed and non-pressure jacketed injectors) have been developed. U.S. Pat. Nos. 5,300,031, 5,779,675, and 5,800,397, for example, disclose front loading, pressure jacketed injector systems and U.S. Pat. No. 5,383,858 discloses front loading, pressure jacketed and non-pressure jacketed injector systems. The contents of U.S. Pat. Nos. 5,300,031, 5,779,675, 5,800,397, and 5,383,858 are incorporated herein by reference.

U.S. Pat. No. 5,300,031 discloses various embodiments of a pressure jacketed injector system wherein a syringe is loaded into and removed from an injector pressure jacket through an opening provided in the front end of the pressure jacket. To retain the syringe within the pressure jacket, for example, during an injection operation, the front end of the syringe is locked to the front end of the pressure jacket.

U.S. Pat. No. 5,779,675 also discloses various embodiments of front loading, pressure jacketed injector systems. In a number of embodiments, for example, as shown in FIGS. 12–16 of the '675 patent, one or more retaining plates or walls, preferably supported by one or more arms or rods, retain a syringe within the pressure jacket. The retaining plates or walls are preferably moved between open and closed positions to allow syringes to be inserted into and removed from the pressure jackets.

While front loading, pressure jacketed injector systems are known in the art, improvements in the design of such pressure jacketed injector systems, and also in the design of syringes used in both pressure jacketed and non-pressure jacketed injector systems, are and continue to be highly desirable.

SUMMARY OF THE INVENTION

The present invention relates generally to a fluid injection apparatus for injecting a fluid medium into an animal. The fluid injection apparatus according to a first embodiment comprises a syringe, an injector, and a front-loading pressure jacket associated with the injector. The syringe comprises a cylindrical shaped body having a distal end and a proximal end. The body has an injection section at the distal end and an outward extending retaining flange at the proximal end. The injector comprises an injector housing defining a central opening and an injector drive piston extendable through the central opening for imparting motive forces to a syringe plunger disposed within the syringe. The front-loading pressure jacket is used to secure the syringe during an injection procedure. The pressure jacket has a distal end and a proximal end. The distal end of the pressure jacket defines a syringe-receiving opening for receiving the syringe into the pressure jacket. The pressure jacket has a wall defining a longitudinally extending groove in an inner surface thereof configured to receive the retaining flange of the syringe. The groove cooperates with a transversely extending slot defined in the inner surface of the pressure jacket wall. To insert the syringe into the pressure jacket, the retaining flange is received in the groove, which guides the syringe into the pressure jacket until the retaining flange reaches the transversely extending slot. Rotational movement of the syringe causes the retaining flange to engage the slot and prevents the syringe from moving distally forward within the pressure jacket.

The groove may extend substantially from the distal end to the proximal end of the pressure jacket and the slot may be located substantially at the proximal end of the pressure jacket. The injection section may include at least one outward extending handle for manipulating the syringe and rotating the syringe in the pressure jacket when the retaining flange is received in the slot. The slot may be configured to permit the syringe to rotate up to about 45° in the pressure jacket when the retaining flange is engaged in the slot. The pressure jacket may be made of substantially clear plastic.

The syringe may comprise a plurality of retaining flanges and the pressure jacket may comprise a plurality of longitudinally extending grooves for receiving the retaining flanges, respectively. The grooves may cooperate, respectively, with a plurality of transversely extending slots defined in the inner surface of the pressure jacket wall. To insert the syringe into the pressure jacket, the grooves may guide the respective retaining flanges into the pressure jacket until the retaining flanges reach the transversely extending slots. Rotational movement of the syringe causes the retaining flanges to engage the slots preventing the syringe from moving distally forward within the pressure jacket. The grooves may extend substantially from the distal end to the proximal end of the pressure jacket and the slots may be located substantially at the distal end of the pressure jacket.

A second embodiment of the present invention relates generally to a pressure jacket assembly for use with the injector. The pressure jacket assembly includes the syringe and the front-loading pressure jacket. The syringe has a cylindrical body with a distal end and a proximal end. The body has an injection section at the distal end and one or more outward extending retaining flanges at the proximal end. The pressure jacket is used to secure the syringe during an injection procedure. The pressure jacket has a distal end and a proximal end. The distal end defines a syringe-receiving opening for receiving the syringe into the pressure jacket. The pressure jacket has a wall defining one or more longitudinally extending grooves in an inner surface thereof configured to receive the retaining flange(s) of the syringe. The groove(s) cooperates with one or more transversely extending slots defined in the inner surface of the pressure jacket wall. To insert the syringe into the pressure jacket, the retaining flange(s) is received in the groove(s), which guides the syringe into the pressure jacket until the retaining flange(s) reaches the transversely extending slot(s). Rotational movement of the syringe causes the retaining flange(s) to engage the slot(s) to prevent the syringe from moving distally forward within the pressure jacket. The pressure jacket assembly may further comprise a syringe plunger located within the syringe body. The syringe plunger may be configured for engagement with an injector drive piston for imparting motive forces to the syringe plunger.

A third embodiment of the present invention relates generally to a syringe that may be used with the pressure jacket assembly and injector described hereinabove. The syringe comprises a body defining a cylindrical main body and a tapering injection section. The injection section is provided at a distal end of the body. The syringe further comprises a plunger movably disposed within at least a portion of the main body. Additionally, the syringe comprises at least one outward extending flange formed on the main body at a proximal end of the body. The retaining flange may be rectangular shaped. The syringe may comprise a plurality of retaining flanges formed on the main body at the proximal end of the body. The retaining flanges may be formed at regular intervals around the circumference of the main body. The plurality of retaining flanges may also be rectangular shaped and oriented on the main body of the syringe to be substantially aligned with and parallel to the longitudinal or central axis of the syringe.

Furthermore, the present invention relates generally to a method of loading a syringe into a front-loading pressure jacket. The syringe may comprise a body defining a cylindrical main body and a tapering injection section. The injection section may be provided at a distal end of the body. A plunger may be movably disposed within at least a portion of the main body. An outward extending flange may be formed on the main body at a proximal end of the body. A pressure jacket assembly may be provided comprising a front-loading pressure jacket associated with an injector. The pressure jacket may have a wall defining a longitudinally extending groove formed in an inner surface thereof for receiving the at least one retaining flange. The groove may cooperate with a transversely extending slot defined in the inner surface of the pressure jacket wall. The method may include the steps of: inserting the proximal end of the body into a distal end of the pressure jacket such that the at least one retaining flange is received in the groove in the inner surface of the pressure jacket wall; guiding the main body into the pressure jacket with the at least one retaining flange received in the groove until the at least one retaining flange reaches the transversely extending slot; and rotating the body in the pressure jacket such that the at least one retaining flange engages the slot to prevent the body from moving distally forward in the pressure jacket. The method may also include the steps of: connecting the plunger to an injector drive piston of the injector; and advancing the injector drive piston to move the plunger in the main body.

The main body may further comprise a plurality of retaining flanges formed at regular intervals around the circumference of the main body. The pressure jacket may further comprise a plurality of longitudinally extending grooves defined in the inner surface of the pressure jacket wall. The grooves may be defined at regular intervals for receiving the flanges, respectively. The grooves may cooperate with a plurality of transversely extending slots defined in the inner surface of the pressure jacket wall. Accordingly, the method may further comprise the steps of: inserting the retaining flanges into the grooves, respectively; guiding the main body into the pressure jacket with the retaining flanges received in the grooves until the retaining flanges reach the transversely extending slots, respectively; and rotating the body in the pressure jacket such that the retaining flanges engage the respective slots to prevent the body from moving distally forward in the pressure jacket.

Further details and advantages of the present invention will become apparent from the following detailed description read in conjunction with the drawings, wherein like parts are designated with like reference characters.

DESCRIPTION OF THE PREFERRED EMBODIMENTS OF THE INVENTION

Figure 1:
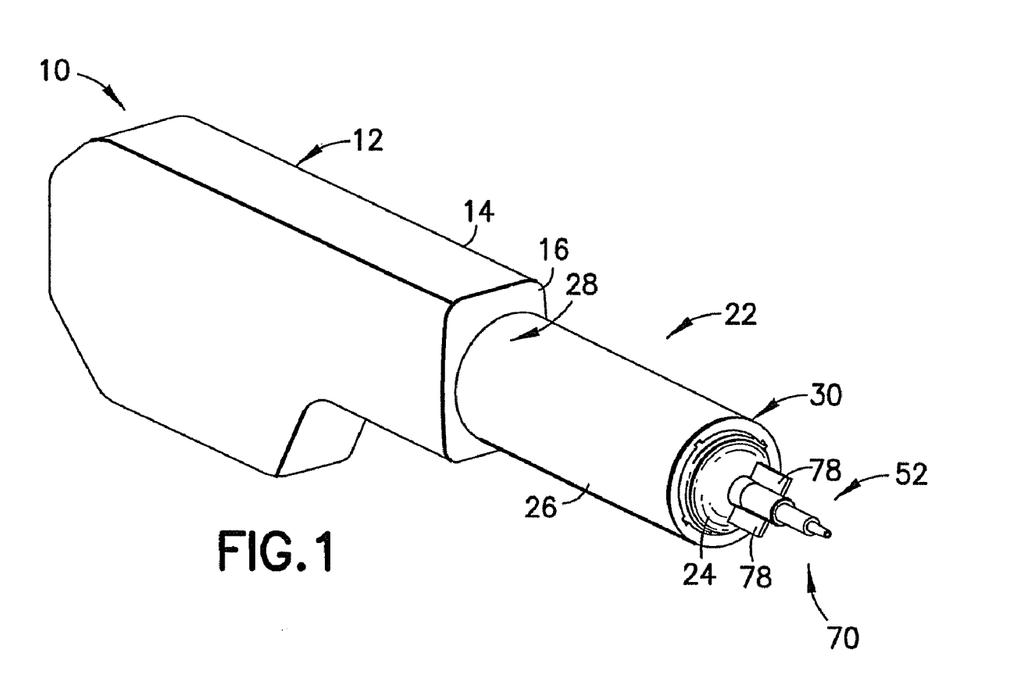
FIG. 1 is a perspective view of a fluid injection apparatus in accordance with an embodiment of the present invention including an injector and a pressure jacket assembly.
Figure 2:
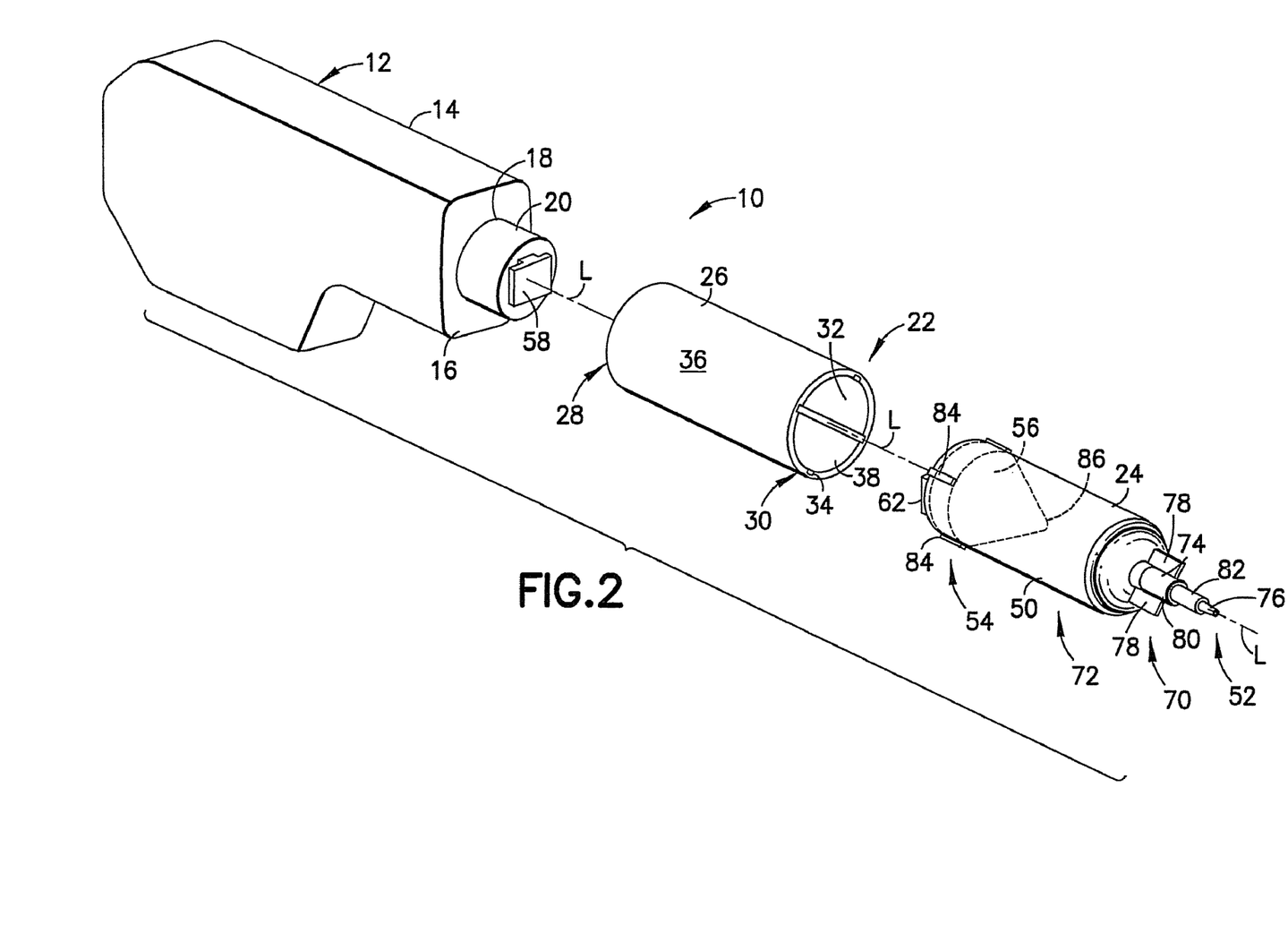
FIG. 2 is an exploded perspective view of the fluid injection apparatus of FIG. 1.
Figure 3:
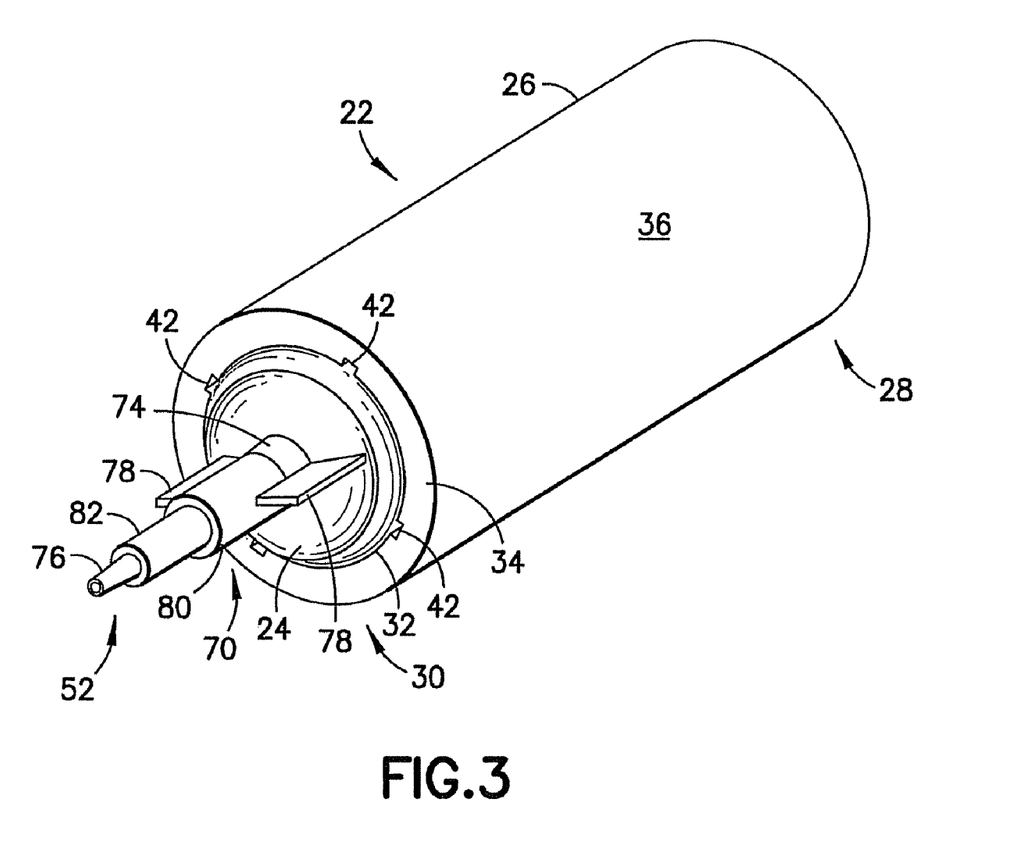
FIG. 3 is a front end perspective view of the pressure jacket assembly of FIG. 1.
Figure 4:
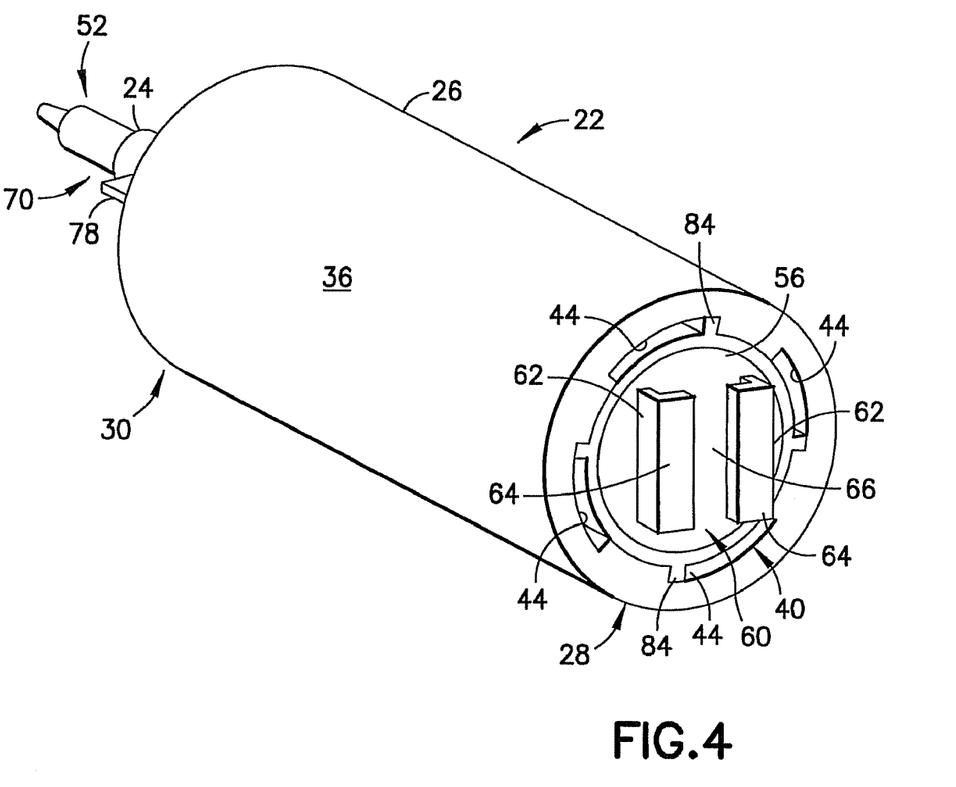
FIG. 4 is a rear end perspective view of the pressure jacket assembly of FIG. 1.
Figure 5:
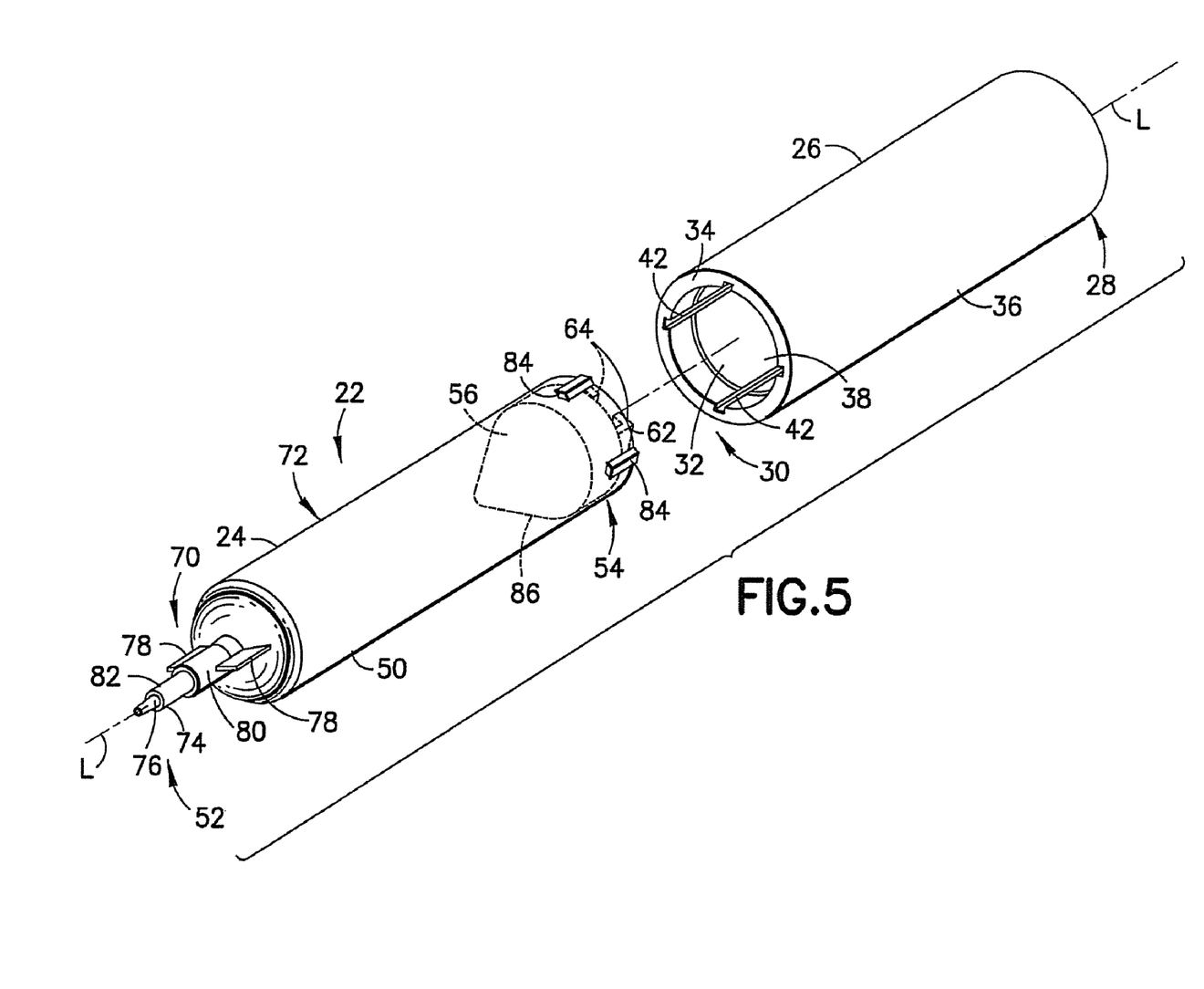
FIG. 5 is an exploded perspective view of the pressure jacket assembly of FIG. 3.
Figures 6, 7:
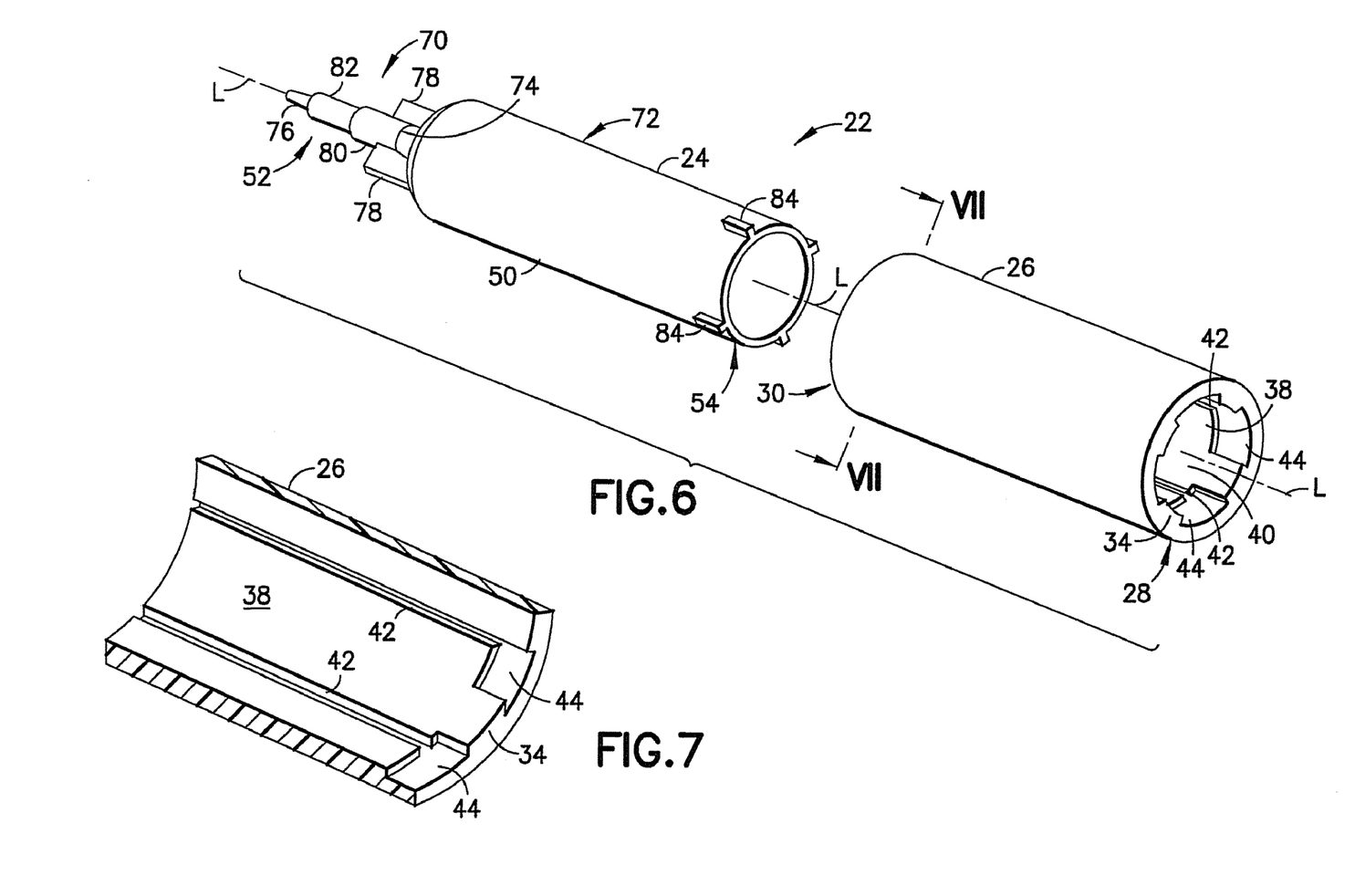
FIG. 6 is an exploded perspective view of the pressure jacket assembly of FIG. 4.
FIG. 7 is a cross sectional view taken along line 7—7 in FIG. 6.

FIGS. 1 and 2 show a fluid injection apparatus 10 in accordance with an embodiment of the present invention. The fluid injection apparatus 10 includes an injector head 12, which may be supported on a support structure (not shown). The injector head 12 includes an injector housing 14 having a front end 16. The front end 16 of the injector housing 14 defines a central opening 18 through which an injector drive piston 20 is extendable and retractable. The details of the injector head 12 and, more particularly, the injector drive piston 20 are described, for example, in U.S. Pat. Nos. 4,677,980 and 5,383,858, which are assigned to the common assignee of this application and which are fully incorporated herein by reference. As described further herein, the injector head 12 is generally used to actuate a syringe 24 used in a fluid injection procedure, such as an angiographic procedure.

The fluid injection apparatus 10 includes a pressure jacket assembly 22, which is associated with the injector head 12. The pressure jacket assembly 22 is comprised of a syringe 24 and a pressure jacket 26. Generally, the pressure jacket assembly 22 extends outward from the front end 16 of the injector housing 14. In particular, the pressure jacket 26 is mounted to the front end 16 of the injector housing 14. The pressure jacket 26 may be mounted to the front end 16 of the injector housing 14 by means customary in the art. Preferably, the pressure jacket 26 is removably mounted to the front end 16 of the injector housing 14. The pressure jacket 26 supports the syringe 24 during a fluid injection procedure. The syringe 24 is received in the pressure jacket 26 in accordance with the features described hereinafter.

Referring now to FIGS. 1–7, the pressure jacket 26 is a generally cylindrical structure having a rear or proximal end 28 and a front or distal end 30. As used in this disclosure, the term "proximal" refers to the injector head 12 facing side of a given element and the term "distal" refers to the syringe 24 facing side of a given element. The distal end 30 of the pressure jacket 26 defines a syringe receiving mouth or opening 32 for receiving the syringe 24 into the pressure jacket 26. The proximal end 28 of the pressure jacket 26 is mounted to the front end 16 of the injector housing 14, and is preferably removably mounted thereto. The pressure jacket 26 has an inner diameter sized to smoothly but snugly receive the outer diameter of the syringe 24.

The pressure jacket 26 is preferably made of a material capable of restraining the outward expansion of the syringe 24 during a fluid injection procedure. As discussed previously, the syringe 24 by itself is typically not capable of withstanding the high pressures associated with certain injection procedures, such as angiography. The pressure jacket 26, as is well known in the art, is used to limit the radial expansion of the syringe 24 which may lead to bursting or leaking as discussed previously. Typically, the syringe 24 is made of a relatively inexpensive medical grade plastic material and is intended to be disposable (i.e., single use). Typical plastics for the syringe 24 include polypropylene, polyethylene, and polycarbonate. The pressure jacket 26 is reusable and made of a material capable of withstanding pressures up to 1200 p.s.i. and higher. For example, the pressure jacket 26 may be made of metal such as steel or aluminum. However, it is advantageous for the syringe 24 to be visible through the pressure jacket 26 so that an operator of the fluid injection apparatus 10 may view the syringe 24 during an injection procedure. Accordingly, the pressure jacket 26 is preferably made of a substantially clear plastic material, such as polycarbonate, for viewing the syringe 24 during an injection procedure.

As stated, the pressure jacket 26 is a generally cylindrical structure. The pressure jacket 26 includes a cylindrical wall 34 that defines the cylindrical structure of the pressure jacket 26. The pressure jacket wall 34 includes an outer surface 36 and an inner surface 38. The proximal end 28 of the pressure jacket 26 is open-ended in a similar manner to the distal end 30. The proximal end 28 of the pressure jacket 26 defines a receiving opening 40 through which the injector drive piston 20 of the injector head 12 may extend to actuate a syringe plunger located within the syringe 24 as discussed further herein. The pressure jacket 26 includes one or more grooves 42 defined in the inner surface 38 of the pressure jacket wall 34. The grooves 42 extend longitudinally along the inner surface 38 of the pressure jacket wall 34. The grooves 42 preferably extend from the distal end 30 of the pressure jacket 26 to the proximal end 28 of the pressure jacket 26. The grooves 42 are provided to guide the syringe 24 into the pressure jacket 26 in the manner discussed hereinafter. The grooves 42 cooperate with a plurality of transversely extending slots 44, respectively. The slots 44 are defined in the inner surface 38 of the pressure jacket wall 34. The slots 44 are preferably formed in the inner surface 38 of the pressure jacket wall 34 substantially at the proximal end 28 of the pressure jacket 26. However, the slots 44 may be formed forwardly of the proximal end 28 of the pressure jacket 26.

The syringe 24 is configured to be received in the pressure jacket 26 through the syringe receiving opening 32 therein. The syringe 24 is generally defined by an elongated, cylindrical syringe body 50 having a distal end 52 and a proximal end 54. A syringe plunger 56 is located in the syringe body 50. The syringe plunger 56 is preferably located at the proximal end 54 of the syringe body 50 prior to actuation by the injector drive piston 20. The syringe plunger 56 is configured for connection to the injector drive piston 20. As mentioned previously, the injector drive piston 20 is extendable through the central opening 18 in the front end 16 of the injector housing 14. The injector drive piston 20 imparts motion to the syringe plunger 56 disposed within the syringe body 50. Accordingly, the injector drive piston 20 is preferably motorized. The injector drive piston 20 includes a rectangular injector end plate 58, which is adapted to engage the syringe plunger 56 and impart motion to the syringe plunger 56. The syringe plunger 56 includes a coupling end 60 that is captured by the injector end plate 58 attached to the injector drive piston 20. The coupling end 60 includes a pair of relatively rigid or flexible lug or coupling members 62 that extend outward from the coupling end 60 for engaging the injector end plate 58 attached to the injector drive piston 20. The coupling members 62 are preferably flexible, as described in U.S. Pat. Nos. 5,873,861 and 5,947,935, the disclosures of which are incorporated herein by reference. The coupling members 62 each have an inward facing engagement arms 64. The coupling members 62 define an engagement slot 66 therebetween. The engagement slot 66 is configured to receive the injector end plate 58 attached to the injector drive piston 20.

The syringe body 50 has an injection section 70 formed at the distal end 52. A generally cylindrical center section or main body 72 is formed adjacent the injection section 70. The center section 72 has a relatively uniform outer diameter. The injection section 70 tapers to form an elongated injection neck 74, which has a relatively small inner diameter compared to the inner diameter of the center section 72. A luer connection 76 may be provided at the distal end of injection neck 74. The injection section 70 may include a pair of outward extending tab members or handles 78. The handles 78 are preferably integrally formed with the syringe body 50. The handles 78 facilitate handling of the syringe 24, including rotation thereof in the pressure jacket 26, as described further herein. The injection section 70 may include a single or multiple conical portions as shown in the figures. The injection section 70 shown in the figures includes a first conical portion 80 connected to the center section 72. A second conical section 82 is connected to the first conical section 80 and located distally forward therefrom. The luer connection 76 is connected to the second conical portion 82. The pressure jacket assembly 22 includes a central axis L, which is also the central axis of the syringe body 50 and the pressure jacket 26. The syringe body 50 is preferably integrally molded as a one-piece unit, with the injection section 70 and center section 72 formed during the molding process.

The proximal end 54 of the syringe body 50 preferably includes one or more raised retaining flanges 84. The retaining flanges 84 are spaced apart around the circumference of the syringe body 50 and, in particular, around the circumference of the center section 72. The retaining flanges 84 are configured to be received within the grooves 42 extending longitudinally in the inner surface 38 of the pressure jacket wall 34. Accordingly, the retaining flanges 84 and the grooves 42 are preferably spaced at mating intervals around the syringe body 50 and within the pressure jacket 26, respectively. The figures of the present disclosure show four retaining flanges 84 configured to cooperate with four longitudinally extending grooves 42. However, any number of retaining flanges 84 and grooves 42 may be used in accordance with the present invention. Only one retaining flange 84 cooperating with a single groove 42 is necessary in the fluid injection apparatus 10 of the present invention. The retaining flanges 84 are generally rectangular shaped and are sized to fit smoothly but snugly within the respective grooves 42. Further, the retaining flanges 84 are preferably oriented to be substantially aligned with and generally parallel to the central axis, L, of the syringe 22 and the pressure jacket assembly 20.

The fluid injection apparatus 10 is used in an injection procedure as generally described hereinafter. The pressure jacket assembly 20 is first mounted to the injector head 12. In particular, the pressure jacket 26 is preferably removably mounted to the front end 16 of the injector housing 14 such that the injector drive piston 20 may extend outward from the injector housing 16 through the central opening 18 and into the receiving opening 40 in the proximal end 28 of the pressure jacket 26. With the pressure jacket 26 mounted in proper registered relationship with the central opening 18 of the injector housing 14, the syringe 24 may be loaded into the pressure jacket 26.

The pressure jacket 26, as will be clear to those skilled in the art, is a front-loading pressure jacket 26 wherein the syringe 24 is loaded into the pressure jacket 26 from the front. To load the syringe 24 into the pressure jacket 26, the retaining flanges 84 are aligned with the grooves 42 in the pressure jacket wall 34. To facilitate the aligning of the retaining flanges 84 with the grooves 42, the operator of the fluid injection apparatus 10 may manipulate the syringe 24 with the handles 78 formed on the injection section 70 of the syringe body 50. Once the retaining flanges 84 are aligned with the grooves 42, the syringe 24 may be moved proximally into the pressure jacket 26. The syringe 24 is moved proximally into the pressure jacket 26 until the retaining flanges 84 coincide with the transversely extending slots 44 formed in the inner surface 38 of the pressure jacket wall 34.

Once the retaining flanges 84 coincide with the slots 44, the operator of the fluid injection apparatus 10 may rotate the syringe 24 within the pressure jacket 26 using the handles 78. For example, the slots 44 may be formed in the pressure jacket wall 34 such that the syringe 24 may be rotated up to about 45° within the pressure jacket 26. Once the retaining flanges 84 are fully engaged in the slots 44, the syringe 24 is restrained from moving distally forward within the pressure jacket 26. Thus, the engagement of the retaining flanges 84 in the slots 44 prevents the syringe 24 from moving distally forward within the pressure jacket 26. As stated previously, the pressure jacket 26 is preferably made of a substantially clear plastic material such that the syringe 24 is visible within the pressure jacket 26 once loaded therein.

After insertion of the syringe 24 into the pressure jacket 26, the injector head 12 may be actuated so that the injector drive piston 20 extends outward from the injector housing 14 and into the pressure jacket assembly 22. The injector drive piston 20, once actuated, extends into the pressure jacket assembly 22 and, more particularly, into the proximal end 54 of the syringe body 50. As the injector drive piston 20 moves forward or distally into the syringe body 50, the injector end plate 58 contacts the engagement arms 64 of the coupling members 62. As the injector drive piston 20 continues to move forward, the injector end plate 58 urges the flexible coupling members 62 apart until the injector end plate 58 is seated in the slot 66 between the coupling members 62, as described in U.S. Pat. Nos. 5,873,861 and 5,947,935. The injector drive piston 20 may then apply motive forces to the syringe plunger 56 to urge the syringe plunger 56 to move distally forward in the syringe body 50 and inject fluid into a patient. The engagement arms 64 secure the engagement between the injector drive piston 20 and the syringe plunger 56 during the procedure. A distal end 86 of the syringe plunger 56 may generally have the conical shape of the injection section 70 of the syringe body 50 so that the syringe plunger 56 cooperates with the conical shape of the injection section 70 once the syringe plunger 56 reaches this position. The injector end plate 58 may be disengaged from the coupling members 62 in the manner described in U.S. Pat. Nos. 5,873,861 and 5,947,935.

While the present invention was described with reference to preferred embodiments, those of ordinary skill in the art may make modifications and alterations to the present invention without departing from the scope and spirit of the invention. Accordingly, the present invention is not intended to be limited to the foregoing detailed description but only by the appended claims and equivalence thereto.

What is claimed is:

1. A fluid injection apparatus, comprising:
a syringe comprising a cylindrical body with a distal end and a proximal end, the body having an injection section at the distal end and at least one outward extending retaining flange at the proximal end;
an injector comprising an injector housing defining an opening and an injector drive piston extendable through the opening for imparting motive forces to a syringe plunger disposed within the syringe; and
a pressure jacket associated with the injector for securing the syringe during an injection procedure, the pressure jacket having a cylindrical shape comprising a distal end and a proximal end, the pressure jacket defining a syringe receiving opening for receiving the syringe into the pressure jacket to encompass a substantial portion of the syringe to restrain outward expansion of the syringe during an injection procedure, the pressure jacket having a wall defining a longitudinally extending groove in an inner surface thereof configured to receive the at least one retaining flange of the syringe, the groove cooperating with a transversely extending slot defined in the inner surface of the pressure jacket wall, wherein to insert the syringe into the pressure jacket the at least one retaining flange is received in the groove, which guides the syringe into the pressure jacket until the at least one retaining flange reaches the transversely extending slot, and wherein rotational movement of the syringe causes the retaining flange to engage the slot, thereby substantially preventing the syringe from moving distally forward within the pressure jacket.

2. The fluid injection apparatus of claim 1, wherein the groove extends substantially from the distal end to the proximal end of the pressure jacket and the slot is located substantially at the proximal end of the pressure jacket.

3. The fluid injection apparatus of claim 1, wherein the injection section includes at least one outward extending handle for manipulating the syringe and rotating the syringe in the pressure jacket when the retaining flange is received in the slot.

4. The fluid injection apparatus of claim 1, wherein the slot is configured to permit the syringe to rotate up to about 45° in the pressure jacket when the retaining flange is engaged in the slot.

5. The fluid injection apparatus of claim 1, wherein the pressure jacket is made of substantially clear plastic.

6. The fluid injection apparatus of claim 1, wherein the syringe comprises a plurality of retaining flanges and the pressure jacket comprises a plurality of longitudinally extending grooves for receiving the retaining flanges, respectively, the grooves cooperating, respectively, with a plurality of transversely extending slots defined in the inner surface of the pressure jacket wall, wherein to insert the syringe into the pressure jacket the grooves guide the respective retaining flanges into the pressure jacket until the retaining flanges reach the transversely extending slots, and wherein rotational movement of the syringe causes the retaining flanges to engage the slots, thereby substantially preventing the syringe from moving distally forward within the pressure jacket.

7. The fluid injection apparatus of claim 6, wherein the grooves extend substantially from the distal end to the proximal end of the pressure jacket and the slots are located substantially at the distal end of the pressure jacket.

8. The fluid injection apparatus of claim 6, wherein the injection section includes at least one outward extending handle for manipulating the syringe and rotating the syringe in the pressure jacket when the retaining flanges are received in the slots.

9. The fluid injection apparatus of claim 6, wherein the slots are configured to permit the syringe to rotate up to about 45° in the pressure jacket when the retaining flanges are engaged in the slots.

10. The fluid injection apparatus of claim 6, wherein the pressure jacket is made of substantially clear plastic.

11. A pressure jacket assembly for use with an injector, comprising:
a syringe comprising a cylindrical body with a distal end and a proximal end, the body having an injection section at the distal end and an outward extending retaining flange at the proximal end; and
a pressure jacket associated with the injector for securing the syringe during an injection procedure, the pressure jacket having a cylindrical shape comprising a distal end and a proximal end, the pressure jacket defining a syringe receiving opening for receiving the syringe into the pressure jacket to encompass a substantial portion of the syringe to restrain outward expansion of the syringe during an injection procedure, the pressure jacket having a wall defining a longitudinally extending groove in an inner surface thereof configured to receive the retaining flange of the syringe, the groove cooperating with a transversely extending slot defined in the inner surface of the pressure jacket wall, wherein to insert the syringe into the pressure jacket the retaining flange is received in the groove, which guides the syringe into the pressure jacket until the retaining flange reaches the transversely extending slot, and wherein rotational movement of the syringe causes the retaining flange to engage the slot, thereby substantially preventing the syringe from moving distally forward within the pressure jacket.

12. The pressure jacket assembly of claim 11, wherein the groove extends substantially from the distal end to the proximal end of the pressure jacket and the slot is located substantially at the proximal end of the pressure jacket.

13. The pressure jacket assembly of claim 11, wherein the injection section includes at least one outward extending handle for manipulating the syringe and rotating the syringe in the pressure jacket when the retaining flange is received in the slot.

14. The pressure jacket assembly of claim 11, wherein the slot is configured to permit the syringe to rotate up to about 45° in the pressure jacket when the retaining flange is engaged in the slot.

15. The pressure jacket assembly of claim 11, wherein the pressure jacket is made of substantially clear plastic.

16. The pressure jacket assembly of claim 11, wherein the syringe comprises a plurality of retaining flanges and the pressure jacket comprises a plurality of longitudinally extending grooves for receiving the retaining flanges, respectively, the grooves cooperating, respectively, with a plurality of transversely extending slots defined in the inner surface of the pressure jacket wall, wherein to insert the syringe into the pressure jacket the grooves guide the respective retaining flanges into the pressure jacket until the retaining flanges reach the transversely extending slots, and wherein rotational movement of the syringe causes the retaining flanges to engage the slots, thereby substantially preventing the syringe from moving distally forward within the pressure jacket.

17. The pressure jacket assembly of claim 16, wherein the grooves extend substantially from the distal end to the proximal end of the pressure jacket and the slots are located substantially at the proximal end of the pressure jacket.

18. The pressure jacket assembly of claim 16, wherein the injection section includes at least one outward extending handle for manipulating the syringe and rotating the syringe in the pressure jacket when the retaining flanges are received in the slots.

19. The pressure jacket assembly of claim 16, wherein the slots are configured to permit the syringe to rotate up to about 45° in the pressure jacket when the retaining flanges are engaged in the slots.

20. The pressure jacket assembly of claim 16, wherein the pressure jacket is made of substantially clear plastic.

21. A method of loading a syringe on an injector, the syringe comprising a body defining a cylindrical main body and a tapering injection section, the injection section provided at a distal end of the body, a plunger movably disposed within at least a portion of the main body, and at least one outward extending retaining flange formed on the main body at a proximal end of the body, and further comprising a pressure jacket assembly comprising a pressure jacket associated with the injector, the pressure jacket having a cylindrical shape to encompass a substantial portion of the syringe to restrain outward expansion of the syringe during an injection procedure, and the pressure jacket comprising a wall defining a longitudinally extending groove formed in an inner surface thereof for receiving the at least one retaining flange, the groove cooperating with a transversely extending slot defined in the inner surface of the pressure jacket wall, the method comprising:

inserting the proximal end of the body into a distal end of the pressure jacket such that the at least one retaining flange is received in the groove in the inner surface of the pressure jacket wall;

guiding the main body into the pressure jacket with the at least one retaining flange received in the groove until the at least one retaining flange reaches the transversely extending slot; and     rotating the body in the pressure jacket such that the at least one retaining flange engages the slot to substantially prevent the body from moving distally forward in the pressure jacket.

22. The method of claim 21, further comprising:

connecting the plunger to an injector drive piston of an injector; and advancing the injector drive piston to move the plunger in the main body.

23. The method of claim 21, further comprising a plurality of retaining flanges formed on the main body at regular intervals around the circumference of the main body, the pressure jacket further comprising a plurality of longitudinally extending grooves formed in the inner surface of the pressure jacket wall, the grooves defined at regular intervals for receiving the retaining flanges, respectively, the grooves cooperating with a plurality of transversely extending slots defined in the inner surface of the pressure jacket wall, the method comprising:

inserting the retaining flanges into the grooves, respectively;

guiding the main body into the pressure jacket with the retaining flanges received in the grooves until the retaining flanges reach the transversely extending slots, respectively; and     rotating the body in the pressure jacket such that the retaining flanges engage the respective slots to substantially prevent the body from moving distally forward in the pressure jacket.

\* \* \* \* \*